(12) United States Patent
Drake, Jr. et al.

(10) Patent No.: US 7,463,363 B2
(45) Date of Patent: Dec. 9, 2008

(54) METHOD AND APPARATUS FOR ULTRASONIC LASER TESTING

(75) Inventors: Thomas E. Drake, Jr., Fort Worth, TX (US); Mark A. Osterkamp, Fort Worth, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 10/634,342

(22) Filed: Aug. 5, 2003

(65) Prior Publication Data

US 2004/0027578 A1  Feb. 12, 2004

Related U.S. Application Data

(63) Continuation of application No. 09/343,920, filed on Jun. 30, 1999, now Pat. No. 6,633,384.

(60) Provisional application No. 60/091,240, filed on Jun. 30, 1998, provisional application No. 60/091,229, filed on Jun. 30, 1998.

(51) Int. Cl.
   *G01B 9/02* (2006.01)
(52) U.S. Cl. ........................ 356/502; 356/432
(58) Field of Classification Search ................. 356/502, 356/493–495, 432
   See application file for complete search history.

(56) References Cited

U.S. PATENT DOCUMENTS

| | | | |
|---|---|---|---|
| 3,911,733 A | 10/1975 | Bhuta et al. | 73/88 |
| 3,992,627 A | 11/1976 | Stewart | 250/312 |
| 4,349,112 A | 9/1982 | Wilks et al. | 209/538 |
| 4,355,538 A | 10/1982 | Hall | 73/811 |
| 4,422,177 A | 12/1983 | Mastronardi et al. | 378/17 |
| 4,803,639 A | 2/1989 | Steele et al. | 364/507 |
| 4,809,308 A | 2/1989 | Adams et al. | 378/99 |
| 4,841,460 A | 6/1989 | Dewar et al. | 364/571.02 |
| 5,014,293 A | 5/1991 | Boyd et al. | 378/198 |
| 5,065,630 A | 11/1991 | Hadcock et al. | 73/802 |
| 5,080,491 A * | 1/1992 | Monchalin et al. | 356/493 |
| 5,113,079 A | 5/1992 | Matulka | 250/550 |
| 5,119,408 A | 6/1992 | Little et al. | 378/4 |
| 5,122,672 A | 6/1992 | Mansour | 250/571 |
| 5,137,361 A * | 8/1992 | Heon et al. | 356/502 |
| 5,140,533 A | 8/1992 | Celette | 364/559 |
| 5,295,073 A | 3/1994 | Celette | 364/424 |
| 5,319,567 A | 6/1994 | Ebenstein | 364/474.34 |
| 5,384,717 A | 1/1995 | Ebenstein | 364/560 |
| 5,442,572 A | 8/1995 | Kiridena et al. | 364/560 |

(Continued)

OTHER PUBLICATIONS

NTIAC Newsletter; vol. 27, No. 5, Sep. 2002, 5 pp.

(Continued)

*Primary Examiner*—Hwa (Andrew) S Lee
(74) *Attorney, Agent, or Firm*—Bracewell & Giuliani LLP

(57) ABSTRACT

The present invention for detecting ultasonic displacements includes a detection laser to generate a first pulsed laser beam to generate the ultrasonic surface displacements on a surface of the target. A seocond pulsed laser beam to detect the ultrasonic surface displacements on a surface of the target. Collection optics to collect phase modulated light from the first pulsed laser beam either reflected or scattered by the target. An interferometer which processes the phase modulated light and generate at least one output signal. A processor that processes the at least one output signal to obtain data representative of the ultrasonic surface displacements at the target.

11 Claims, 10 Drawing Sheets

U.S. PATENT DOCUMENTS

| | | | | |
|---|---|---|---|---|
| 5,490,195 | A | 2/1996 | Berkley | 378/72 |
| 5,541,856 | A | 7/1996 | Hammermeister | 364/552 |
| 5,552,984 | A | 9/1996 | Crandall et al. | 364/424.03 |
| 5,574,226 | A | 11/1996 | Reuther et al. | 73/669 |
| 5,637,812 | A | 6/1997 | Baker et al. | 73/865.6 |
| 5,706,094 | A * | 1/1998 | Maris | 356/432 |
| 5,848,115 | A | 12/1998 | Little et al. | 378/4 |
| 6,008,887 | A * | 12/1999 | Klein et al. | 356/28.5 |
| 6,023,985 | A | 2/2000 | Fournier | 73/865.6 |
| 6,047,041 | A | 4/2000 | Ellinger | 378/58 |
| 6,108,087 | A * | 8/2000 | Nikoonahad et al. | 356/503 |
| 6,128,081 | A * | 10/2000 | White et al. | 356/503 |
| 6,181,431 | B1 * | 1/2001 | Siu | 356/502 |
| 6,205,240 | B1 | 3/2001 | Pietrzak et al. | 382/152 |
| 6,220,099 | B1 | 4/2001 | Marti et al. | 73/633 |
| 6,360,621 | B1 | 3/2002 | Eldred et al. | 73/865.6 |
| 6,378,387 | B1 | 4/2002 | Froom | 73/865.8 |
| 6,466,643 | B1 | 10/2002 | Bueno et al. | 378/58 |
| 6,571,008 | B1 | 5/2003 | Bandyopadhyay et al. | 382/154 |
| 6,637,266 | B1 | 10/2003 | Froom | 73/583 |

OTHER PUBLICATIONS

Froom, Douglas A., et al.; Solving Problems with Advanced Technology, 1999 IEEE, 4 pp.

Alkire, M.G., Department of the Air Force Memo regarding Construction Project Data; May 7, 1982, Bates 000010 through Bates 000068.

U.S. Air Force, Military Construction Project Data, Apr. 14, 1982, Bates 000074 through Bates 000129.

U.S. Air Force, Attachment I to Request for Environmental Impact Analysis, Dec. 2, 1982, Bates 000130 through Bates 000167.

Stanghellini, Frank D., Department of the Air Force Memo regarding Criteria Changes, Jan. 9, 1985, Bates 000168 through Bates 000214.

Metro Today, The Sacramento Union; May 12, 1983, Bates 000215 through Bates 000216.

Letter Contract Between Department of the Air Force and Par Systems Corp., Aug. 3, 1984, Bates 000217 through Bates 000312.

Timeline and Equipment List for Contract Between Department of the Air Force and Par Systems Corp., Aug. 3, 1984, Bates 000313 through Bates 000325.

Spacemaker, Jun. 19, 1997, Bates 000326 through 000327.

Civilian Personnel Position Description, Department of the Air Force; Jul. 10, 1989, Bates 000328 through Bates 000332.

Aviation Week & Space Technology, Mar. 13, 1989, Bates 000333 through Bates 000336.

UltraOptec, Laser Ultrasonic System, 1999 IEEE Bates 000337 through Bates 000340.

J.W. Bader, et al., Laser Ultrasonics or Alternative NDI Composite Defect, Nov. 20, 1990, Bates 000342 through Bates 000446.

Douglas A. Froom, Statement of Work for Advanced Ultrasonic Component Inspection System, Jul. 14, 1993, Bates 000447 through 000490.

Award of Contract from Department of the Air Force, Aug. 11, 1993, Bates 000491 through Bates 000492.

UltraOptec, LUIS Phase 3 Acceptance Test Report, Feb. 16, 1996, Bates 000493 through Bates 000501.

Spacemaker, Feb. 22, 1996, Bates 000502.

* cited by examiner

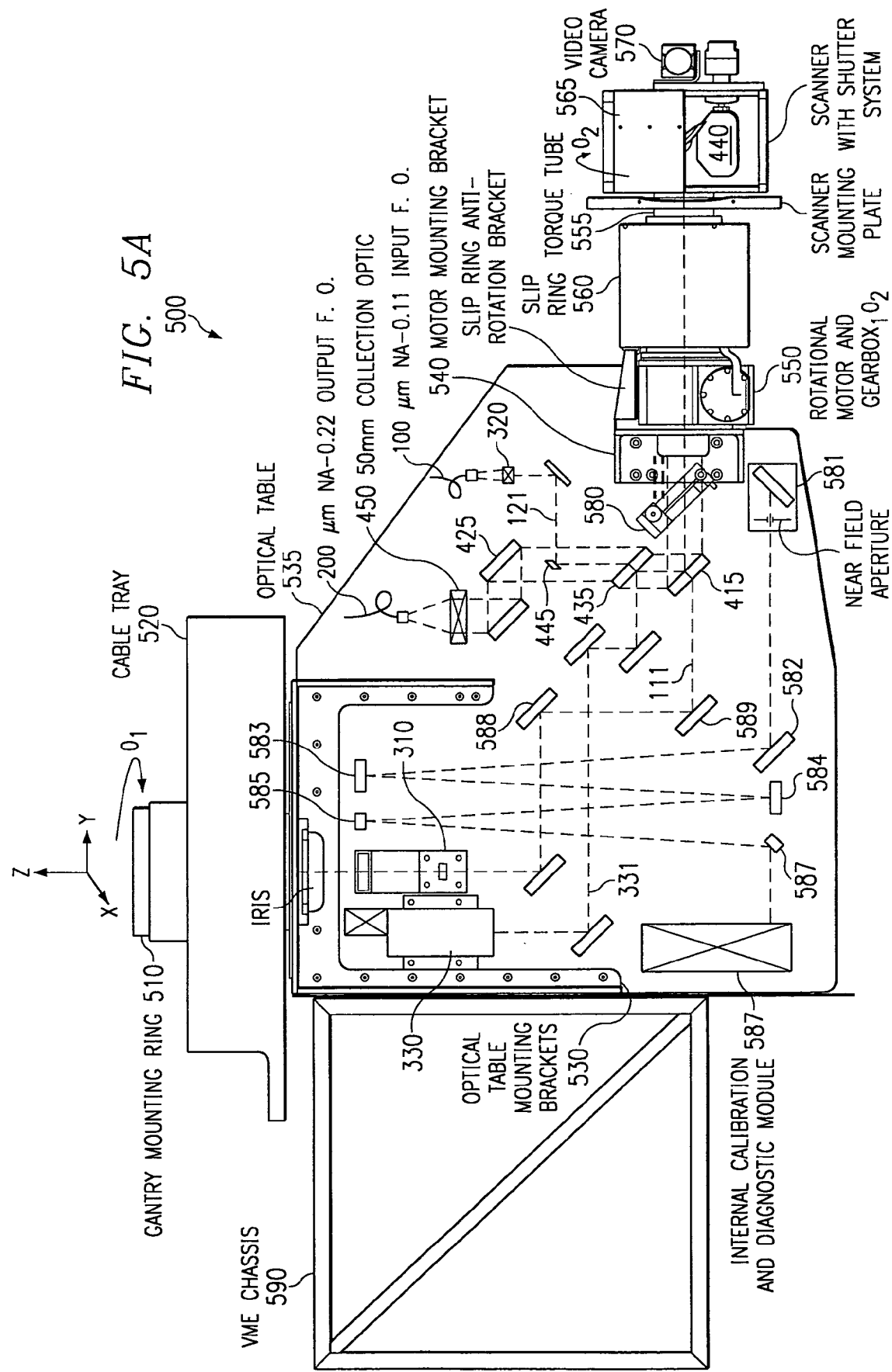

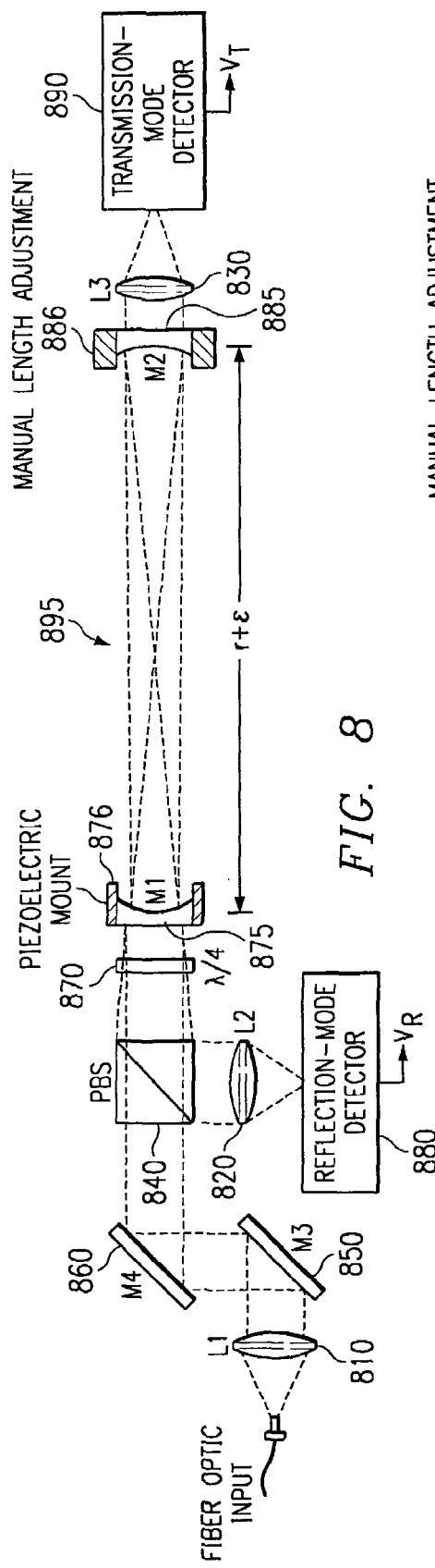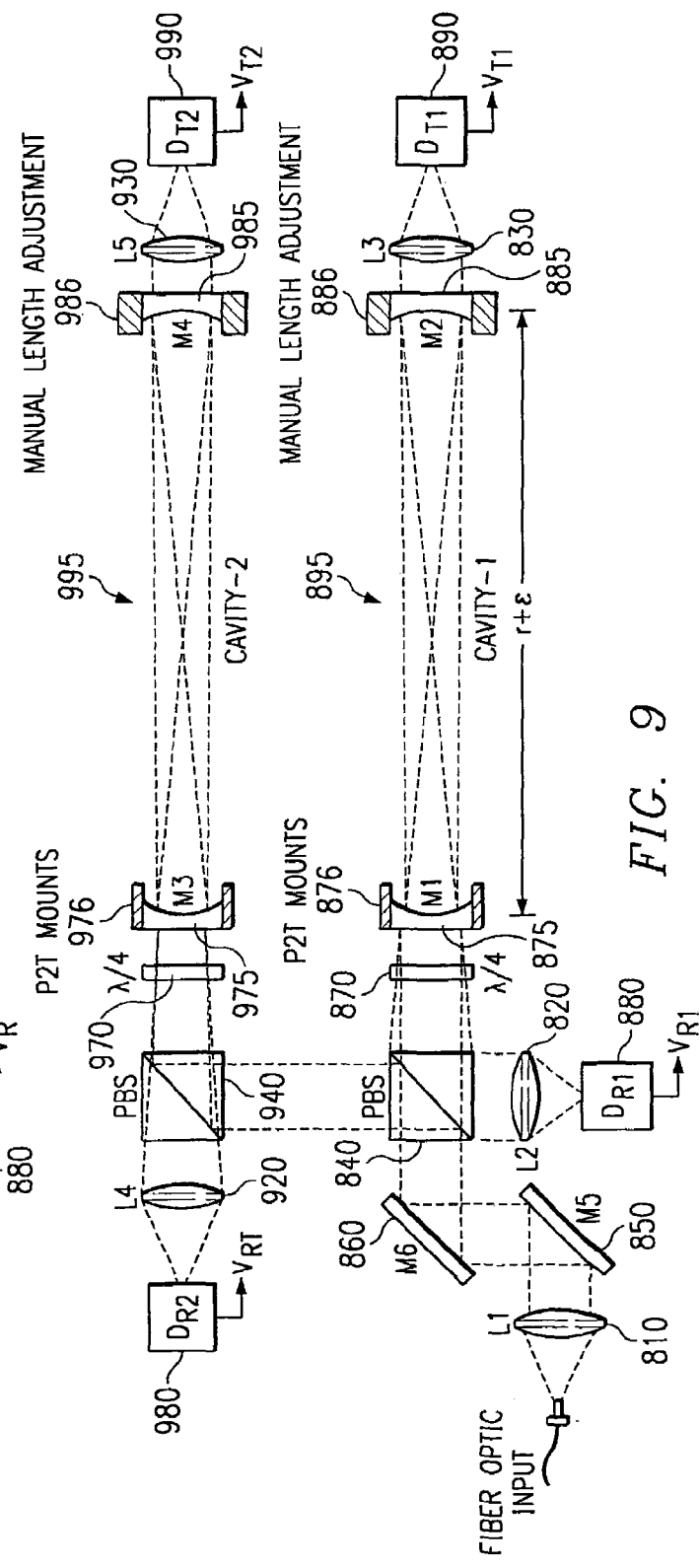

METHOD AND APPARATUS FOR ULTRASONIC LASER TESTING

RELATED APPLICATIONS

This application is a continuation of U.S. patent application No. 09/343,920 filed Jun. 30, 1999 now U.S. pat. No. 6,633,384 entitled, "METHOD AND APPARATUS FOR ULTRASONIC LASER TESTING", which claims the benefit of U.S. Provisional application No. 60/091,240 filed on 30 Jun. 1998, and incorporates by reference the prior of U.S. Provisional Application No. 60/091,229 filed on 30 Jun. 1998 entitled, METHOD AND APPARATUS FOR DETECTING ULTRASONIC SURFACE DISPLACEMENTS USING POST-COLLECTION OPTICAL AMPLIFICATION by Thomas E. Drake.

TECHNICAL FIELD OF THE INVENTION

The present invention relates generally to an apparatus and method of non-destructive evaluation of materials, and more particularly, to an apparatus and method of processing optical information to detect ultrasonic surface displacements through the use of at least one laser to perform a non-destructive evaluation of a material.

BACKGROUND OF THE INVENTION

In recent years, the use of advanced composite structures has experienced tremendous growth in the aerospace, automotive, and many other commercial industries. While composite materials offer significant improvements in performance, they require strict quality control procedures in the manufacturing processes. Specifically, non-destructive evaluation ("NDE") methods are required to assess the structural integrity of composite structures, for example, to detect inclusions, delaminations and porosities. Conventional NDE methods, however, are very slow, labor-intensive, and costly. As a result, testing procedures adversely increase the manufacturing costs associated with composite structures.

Various methods and apparatuses have been proposed to assess the structural integrity of composite structures. One method to generate and detect ultrasound using lasers is disclosed in U.S. Pat. No. 5,608,166, issued Mar. 4, 1997, to Monchalin et al. (the "'166 Patent"). The '166 Patent discloses the use of a first modulated, pulsed laser beam for generating ultrasound on a work piece and a second pulsed laser beam for detecting the ultrasound. Phase modulated light from the second laser beam is then demodulated to obtain a signal representative of the ultrasonic motion at the surface of the work piece. A disadvantage associated with this approach is that the first pulsed laser beam must be modulated. Other U.S. patents issued to Monchalin et al. and relating to the subject matter of ultrasonic material testing include the following:

| U.S. Pat. No. | Title | Issue Date |
| --- | --- | --- |
| 5,608,166 | Generation and Detection of Ultrasound with Long Pulse Lasers | Mar. 4, 1997 |
| 4,966,459 | Broadbank Optical Detection of Transient Motion from a Scattering Surface | Oct. 30, 1990 |
| 5,131,748 | Broadbank Optical Detection of Transient Motion from a Scattering Surface by Two-Wave Mixing in a Photorefractive Crystal | Jul. 21, 1992 |
| 5,402,235 | Imaging of Ultrasonic-Surface Motion by Optical Multiplexing | Mar. 29, 1995 |
| 4,633,715 | Laser Heteroclyne Interferometric Method and Apparatus for Measuring Ultrasonic Displacements | Jan. 6, 1987 |
| 5,080,491 | Laser Optical Ultrasound Detection Using Two Interferometer Apparatuses | Jan. 14, 1992 |
| 5,137,361 | Optical Detection of a Surface Motion of an Object Using a Stabilized Interferometric Cavity | Aug. 11, 1992 |
| 4,426,155 | Method and Apparatus for the Interferometric Wavelength Measurement of Frequency Tunable C.W. Lasers | Jan. 17, 1984 |
| 5,608,166 | Generation and Detection of Ultrasound with Long Pulse Lasers | Mar. 4, 1991 |
| 4,820,981 | Method and Apparatus for Measuring Magnetic Losses in Ferromagnetic Materials Based on Temperature Modulation Measurements | Apr. 11, 1989 |
| 4,659,224 | Optical Interferometric Reception of Ultrasonic Energy | Apr. 21, 1987 |
| 4,607,341 | Device br Determining Properties of Materials from a Measurement of Ultrasonic Absorption | Aug. 19, 1986 |

Although these patents describe operable techniques for optically detecting transient motion from a scattering surface, which techniques are useful for ultrasonic composite materials non-destructive test and evaluation, these techniques have numerous failings.

To begin, none of the Monchalin and other known techniques provide the ability to perform with high signal-to-noise-ratios (SNR) at large distances from typically very dark composite materials using small aperture high-speed optical scanning methods. The ability to operate in such a mode has the distinct advantage of increasing the optical scan area coverage and providing substantially improved depth-of-field thereby eliminating the need for active focusing mechanisms.

Other known techniques do not posses the desirable feature of removing common-mode noise from the laser signals using a fully self-referenced interferometric configuration that uses all of the available light without the use of separate stabilization measurements.

Another limitation associated with the Monchalin and other known apparatuses relates to their inability to operate at very high scan rates and process ultrasonic data in real-time. This limitation makes such apparatuses only marginally useful for testing and evaluating composite materials.

Other limitations associated with existing apparatuses relate to general inflexibility of such apparatuses, which may hold all distances low, result in small depth of field performance and only minimal extraction of information from the back scattered signals. These limitations make industrial application of the ultrasonic testing method generally impractical.

SUMMARY OF THE INVENTION

The present invention provides an apparatus and method for generating and detecting ultrasonic surface displacements on a remote target that substantially eliminates or reduces disadvantages and problems associated with previously developed laser ultrasonic systems and methods.

More specifically, the present invention provides a method and system for generating and detecting ultrasonic surface displacements on a remote target. The system includes a first pulsed laser to generate a first pulsed laser beam. The first pulsed laser beam produces ultrasonic surface displacements on a surface of the remote target. A second pulsed laser generates a second pulsed laser beam coaxial with said first pulsed laser beam to detect the ultrasonic surface displacements on the surface of the remote target. Collection optics to collect phase modulated light from the second pulsed laser beam either reflected or scattered by the remote target and optionally optically processed to increase the light intensity. An interferometer to process the phase modulated light and generate at least one output signal. A processor for processing the at least one output signal obtains data representative of the ultrasonic surface displacements on the surface of the remote target.

In another embodiment, a method for ultrasonic laser testing in accordance with the invention comprises using a first pulsed laser beam to generate ultrasonic surface displacements on a surface of a remote target. A second pulsed laser beam coaxial is used with the first pulsed laser beam to detect the ultrasonic surface displacements on the surface of the remote target collecting phase modulated light from the second pulse laser beam either reflected or scattered by the remote target also occurs, processing the phase modulated light to obtain data representative of the ultrasonic surface displacements on the surface of the remote target.

A technical advantage of the present invention is that a method for ultrasonic laser testing is provided. The personal invention provides rapid, non-contact, and non-destructive inspection techniques that can be applied to complex composite structures. The present invention provides a flexible, accurate and cost effective method for inspecting complex composite structures. The present invention is able to rapidly scan and test large-sized composite structures. The present invention is able to inspect at angles off normal (i.e., up to ±45 degrees). The present invention does not require expensive fixturing to test composite structures. The present invention does not require the shape of the part to be known prior to testing. The present invention does not require access to both sides of a composite structure to test it for defects.

BRIEF DESCRIPTION OF THE DRAWINGS

For a more complete understanding of the present invention, the objects and advantages thereof, reference is now made to the following descriptions taken in connection with the accompanying drawings in which:

FIG. 5A presents a gantry mounted optical test apparatus with an internal calibration unit;

FIG. 8 is a modified, single cavity confocal Fabry-Perot type interferometer;

FIG. 9 is a modified, dual cavity confocal Fabry-Perot type interferometer;

DETAILED DESCRIPTION OF THE INVENTION

Preferred embodiments of the present invention are illustrated in FIGS. 1 through 17 of the drawings, like numerals being used for like and corresponding parts of the various drawings.

Figure 1:
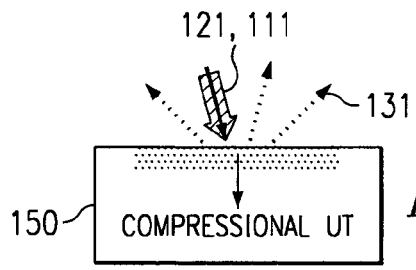
FIG. 1 illustrates the use of a generation laser beam and a detection laser beam coaxial therewith.

FIG. 1 illustrates an incoming laser beam which represents a generation laser beam 111 and a coaxial detection laser beam 121 upon a remote target 150. Generation laser beam 111 causes thermoelastic expansion in the target 150 in the form of ultrasonic surface deformations, which deformations modulate, scatter and reflect detection laser beam 121, represented by the phase-modulated light 131 directed away from target 150.

Figure 2:
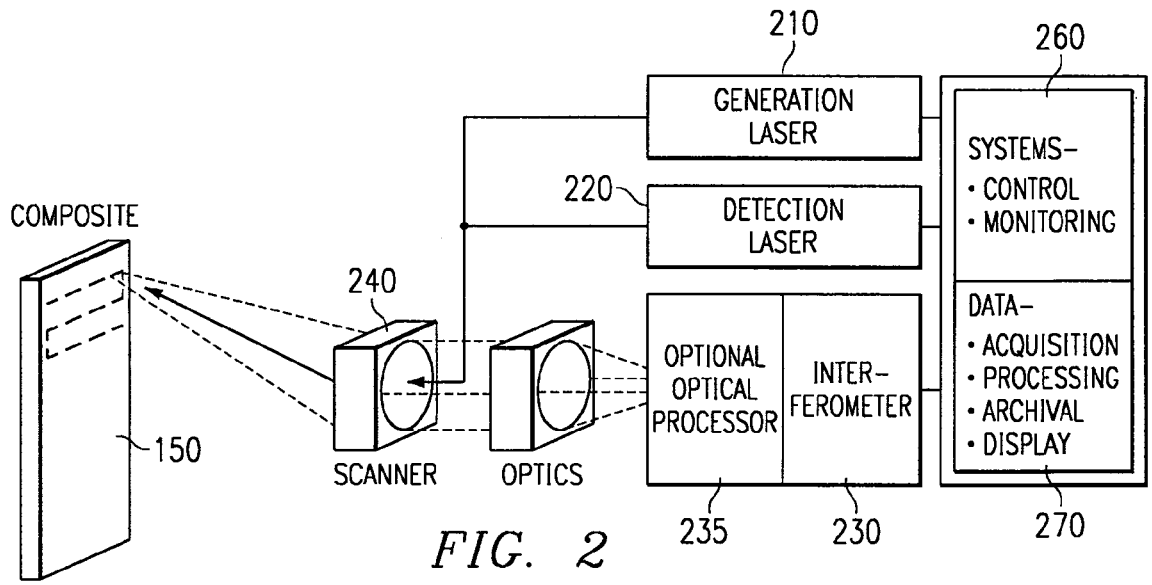
FIG. 2 is a block diagram showing the basic components of an apparatus for performing ultrasonic laser testing.

FIG. 2 illustrates in block diagram form the basic components of an apparatus 200 for performing ultrasonic laser testing. Apparatus 200 comprises a generation laser 210, a detection laser 220, an interferometer 230, an optional optical processor 235, an optical scanner 240, collection optics 250, systems controller 260, and data acquisition and processing apparatus 270. Generation laser 210 and detection laser 220 generate a generation laser beam 111 and a detection laser beam 121, respectively, which are directed by optical scanner 240 upon a target 150, which is typically a composite material. The generation laser 210 produces a compressional ultrasonic wave in the material normal to the surface of the target 150. The compressional ultrasonic wave is the result of thermoelastic expansion of the composite material as it absorbs generation laser beam 111.

The generation laser 210 must be of a frequency that is readily absorbed into the surface of target 150 without causing ablation or breaking down the target material, and it must be of the appropriate pulse duration to induce ultrasonic surface deformations. For example, a transverse-excited atmospheric ("TEA") $CO_2$ laser can be used to produce a 10.6 micron wavelength beam for a 100 nanosecond pulse. The power of the laser must be sufficient to deliver, for example, a 0.25 joule pulse to the target, which may require a 100 watt laser operating at a 400 Hz pulse repetition rate. The generation laser should be absorbed as heat into the target surface thereby causing thermoelastic expansion without ablation.

The detection laser 220 must be of sufficient pulse duration to not induce ultrasonic surface displacements. For example, a Nd:YAG laser can be used. The power of this laser must be sufficient to deliver, for example, a 100 milli-joule, 100 micro-second pulse, which may require a one kilo-watt laser.

Figure 3:
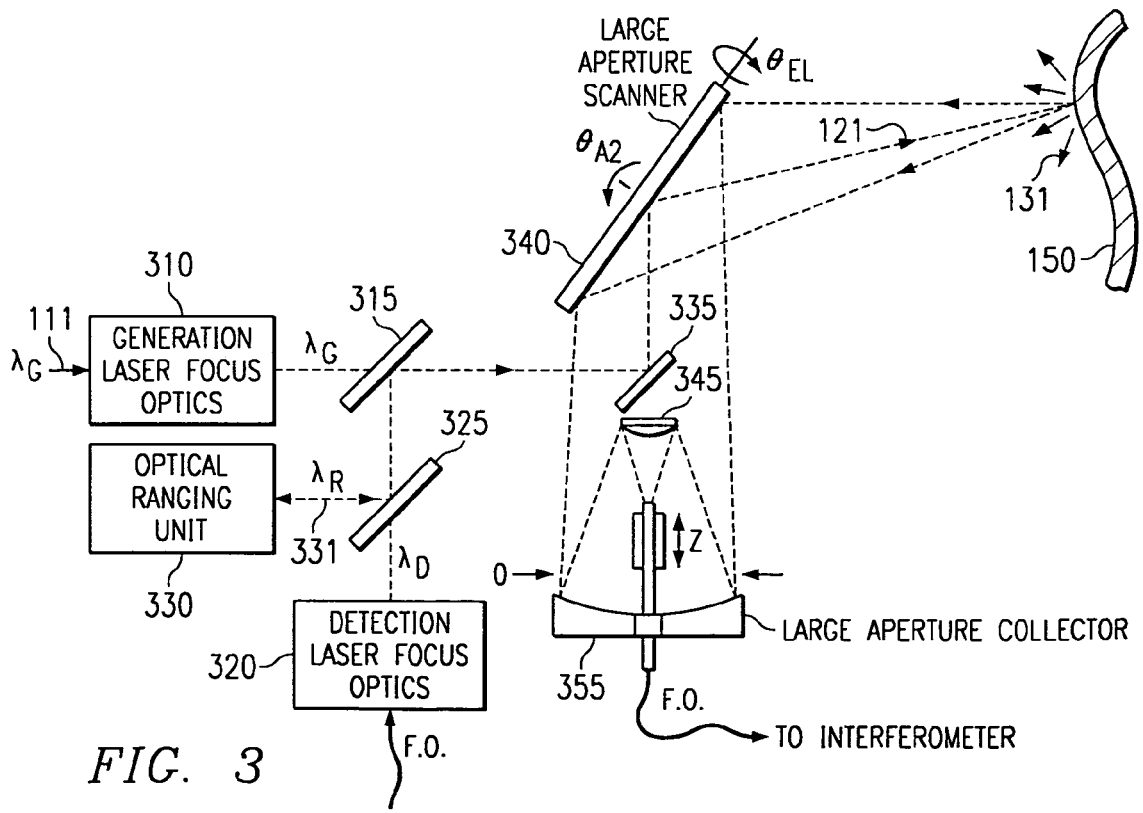
FIG. 3 presents a large aperture optical scanner.

FIG. 3 illustrates a large aperture optical scanning configuration with an integrated distance ranging unit. Generation laser beam 111 is focused by generation laser focus optics 310 through a first optical lens assembly 315 which is transmissive to generation laser beam 111. Reflective surface 335 then directs generation laser beam 111 upon large aperture scanner 340 which, in turn, directs said beam 111 upon a surface of target 150, which induces an ultrasonic wave therein.

As shown in FIG. 3, detection laser beam 121 is directed by fiber optics into detection laser focus optics 320, which focuses laser beam 121 through a second optical lens 325 which is transmissive to detection laser beam 121. Detection laser beam 121 is reflected off first optical lens 315 and emerges coaxial with generation laser beam 111. First optical assembly 315 and second optical assembly 325 act collectively to form a beam combiner or beam mixer. Detection laser beam 121 is then reflected along with generation laser beam 111 upon a turning mirror or a reflective surface 335, which then directs detection laser beam 121 upon large aperture scanner 340 which, in turn, directs said beam 121 upon the surface of target 150. Detection laser beam 121 interacts with the ultrasonic waves present in the surface of target 150, and is reflected as phase modulated light 131. Some of the phase modulated light is captured by large aperture scanner 340 and is directed upon large aperture collector 350. Large aperture scanner 340 is generally of the single-mirror two-axis gimbal construction with each axis driven via a motor and gear assembly. Large aperture collector 350 may be of a Cassegrain-type reflective optic, comprised of a primary reflective surface 355 which focuses light upon a secondary reflective surface 345, which in turn, collects the light and focuses it into a fiber optic carrier.

FIG. 3 also illustrates the integrated optical ranging unit 330 which directs a ranging laser beam 331 upon optical lens 325 which reflects said laser beam 331 upon first optical lens 315. Ranging laser beam 331 emerges coaxial with generation laser beam 111 and detection laser beam 121. Ranging laser beam 331 is then reflected along the same path as detection laser beam 121 and also is reflected from the surface of target 150. Some of the reflected ranging laser is captured by large aperture scanner 340 and directed backwards upon the same path which it traveled to reach target 150. Scanner 340, collection optics 345 and 355 are generally defined as of the large aperture type for beam clear apertures larger than approximately 75 mm for distances to the target in the 1000 mm to 4000 mm range. Optical ranging unit 330 is able to determine from the reflected light the distance between the surface of the target 150 being illuminated and the scanning apparatus. Because optical ranging unit 330 both transmits and receives light of the same frequency, it is described as a self-contained ranging apparatus. It is important to know the distance by which the surface being illuminated is located from the scanner so that a topographical contour can be created for target 150 and correlated to the optical data being collected. Generally, this correlation is recorded on a point-by-point basis.

Figure 4:
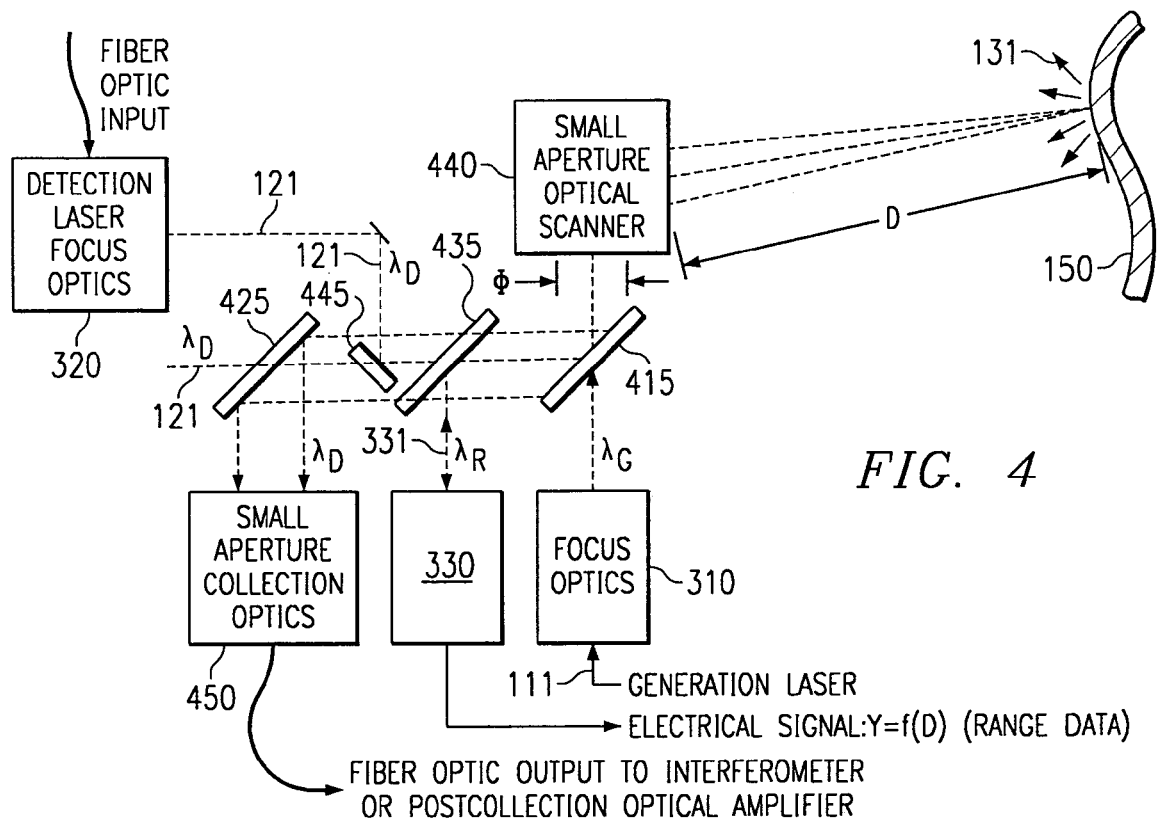
FIG. 4 presents a small aperture optical scanner.

FIG. 4 illustrates a small aperture optical scanning configuration with an integrated distance ranging unit. Small aperture is generally defined, in this application, for clear apertures less than 75 mm for target distances between 1000 mm and 4000 mm. The operation of the small aperture configuration is similar to that of the large aperture optical scanning configuration previously discussed with a slight rearrangement of the optical elements to accommodate the laser beams through the smaller apertures. Generation laser beam 111 is focused by generation laser focus optics 310 through a first optical element 415 to small aperture scanner 440, where in the optical element 415 is transmissive to generation laser beam 111. Small aperture scanner 440, in turn, directs said beam 111 upon a surface of target 150, which induces an ultrasonic wave therein. Small aperture scanner 440 is generally of two-mirror construction with each mirror mounted on orthogonal oriented high-speed galvanometers.

As shown in FIG. 4, detection laser beam 121 is directed by fiber optics into detection laser focus optics 320, which directs laser beam 121 to a small reflective turning mirror 445 and through optical element 435, which is transmissive to detection laser beam 121. Detection laser beam 121 is reflected off first optical element 415 and emerges coaxial with generation laser beam 111. Reflective turning mirror 455 is generally of elliptical profile so as to produce a small circular diameter exactly matching detection laser beam 121 when operated at 45 degrees angle of incidence, and thereby obscuring a minimal amount of collection optic 450. First optical element 415, second optical element 425, and third optical element 435 collectively act to form a beam combiner or beam mixer. Detection laser beam 121 is then reflected along with generation laser beam 111 upon small aperture scanner 440 which, in turn, directs said beam 121 upon the surface of target 150. Detection laser beam 121 interacts with the ultrasonic waves present in the surface of target 150, and is reflected as phase-modulated light 131. Some of phase modulated light 131 is captured by small aperture scanner 440 and is reflected off first optical element 415, through third optical element 435, and reflected off second optical element 425 into small aperture collector 450. Optical element 445 will, by proper design, obscure a minimal portion of the light captured by scanner 440.

FIG. 4 also illustrates the integrated optical ranging unit 330 which directs a ranging laser beam 331 upon third optical element 435 which reflects laser beam 331 upon first optical element 415. Ranging laser beam 331 emerges coaxial with generation laser beam 111 and detection laser beam 121. Ranging laser beam 331 is then reflected along the same path as detection laser beam 121 and also gets reflected from the surface of target 150. Some of the reflected ranging laser is captured by small aperture scanner 440 and directed backwards upon the same path which it traveled to reach target 150. Optical ranging unit 330 is able to determine from the reflected light the distance between the scanning apparatus and the surface of the target 150 being illuminated. The distance between the scanning apparatus and the surface being illuminated is used to create a topographical contour of the target 150 being scanned, and is correlated to the optical data being collected. Generally, this correlation is recorded on a point-by-point basis.

FIG. 5A illustrates a portion of a laser scanning and test apparatus 500, referred to as "scan head 500", that is typically, although not exclusively, mounted to a gantry positioning system (GPS) capable of indexing said apparatus throughout a Cartesian work volume defined by {x,y,z}. Generation laser 110 may be remotely located on the GPS, or alternatively ground mounted and directed along the x and y axis, and eventually directed concentric with the z-mast assembly through gantry mounting ring 510. Another embodiment of said invention would allow delivery of generation laser 210 laser beam 111 through an optical fiber. Fiber optic delivery of laser beam 111 would allow generation laser 210 to be remotely located or optionally mounted within scan head 500. Scan head 500 can be rotated concentric to the z-axis defined as theta-1 to reposition the orientation of the optical table mounting bracket 530 and optical table 535. Cable tray 520 provides electrical, optical, and other connections to 500 allowing 360-degree rotation of theta-1. Bracket 540 attaches motor 550 to optical table 535. Motor 550 rotates optical scanner 440 via torque tube 555 concentric with the optical axis, defined as the theta-2 axis. Slip ring 560 provides electrical connections between VME chassis 590 and components mounted to the theta-2 axis, including optical scanner 440, scanner shutter 565, and remote video camera 570. Scanner shutter 560 protects optical scanner 440 from dust contamination when not in use. Remote video camera 570 provides the operator at a distant location a view nearly aligned with the center view of scanner 440. Detection laser light 121 is collected from a remote composite surface located some distance D from the small-aperture optical scanner 440 and is reflected by element 415, transmitted by element 435, and is minimally obscured by mirror 445. Next 121 is directed by mirror 425, and other turning mirrors, onto small-aperture collector 450, and subsequently coupled into the collection fiber optic. This collection fiber is typically coupled to a post-collection optical amplifier 235 (FIG. 2) prior to processing by interferometer 230.

Motorized mirror mount 580 provides a method to redirect the optical path for all of the laser beams beyond optical element 415 but prior to optical scanner 440. Said redirected beams follow a path along a series of reflective turning mirrors 581, 582, 583, 584, 585, and 586 to an internal far-field calibration module 587, the number of turning mirrors is only representative of the desired function, where the actual number could be more or less. Tuning mirror 581, for example, would have an integrated near field adjustable aperture to establish a permanent alignment position to be used in conjunction with the internal far-field calibration module 587. Far-field calibration module 587 is located a distance from optical element 415 to be representative of a typical distance to a target following the standard path through optical scanner 440. Internal far-field calibration and diagnostic module 587 may contain, as example, devices to monitor the power and alignment of each laser, small targets representative of typical testing materials, and devices to assist in the characterization of new materials over a variety of incident angles. As an example, information derived from the internal far-field calibration and diagnostic module 587 could be used to align the generation laser beam 111 to the desired optic axis via motorized reflective tuning mirrors 588 and 589. Such an operation may be necessary to correct for small beam delivery errors created by the remote free-space delivery of beam 111 along the movable axis {x,y,z,theta-1}. Other turning mirrors, not explicitly specified in FIG. 5a, may also incorporate motorized positioning features similar to 588 and 589 as required to allow a fully automated alignment and calibration procedure to be executed under computer control. All alignment procedures are generalized in that the motorized mirror nearest the far-field calibration module is adjusted for proper alignment, then the motorized mirror farthest from the near-field aperture is adjusted for alignment. This procedure is continued in an iterative manner until an allowable amount of positioning error is reached.

Figure 5B:
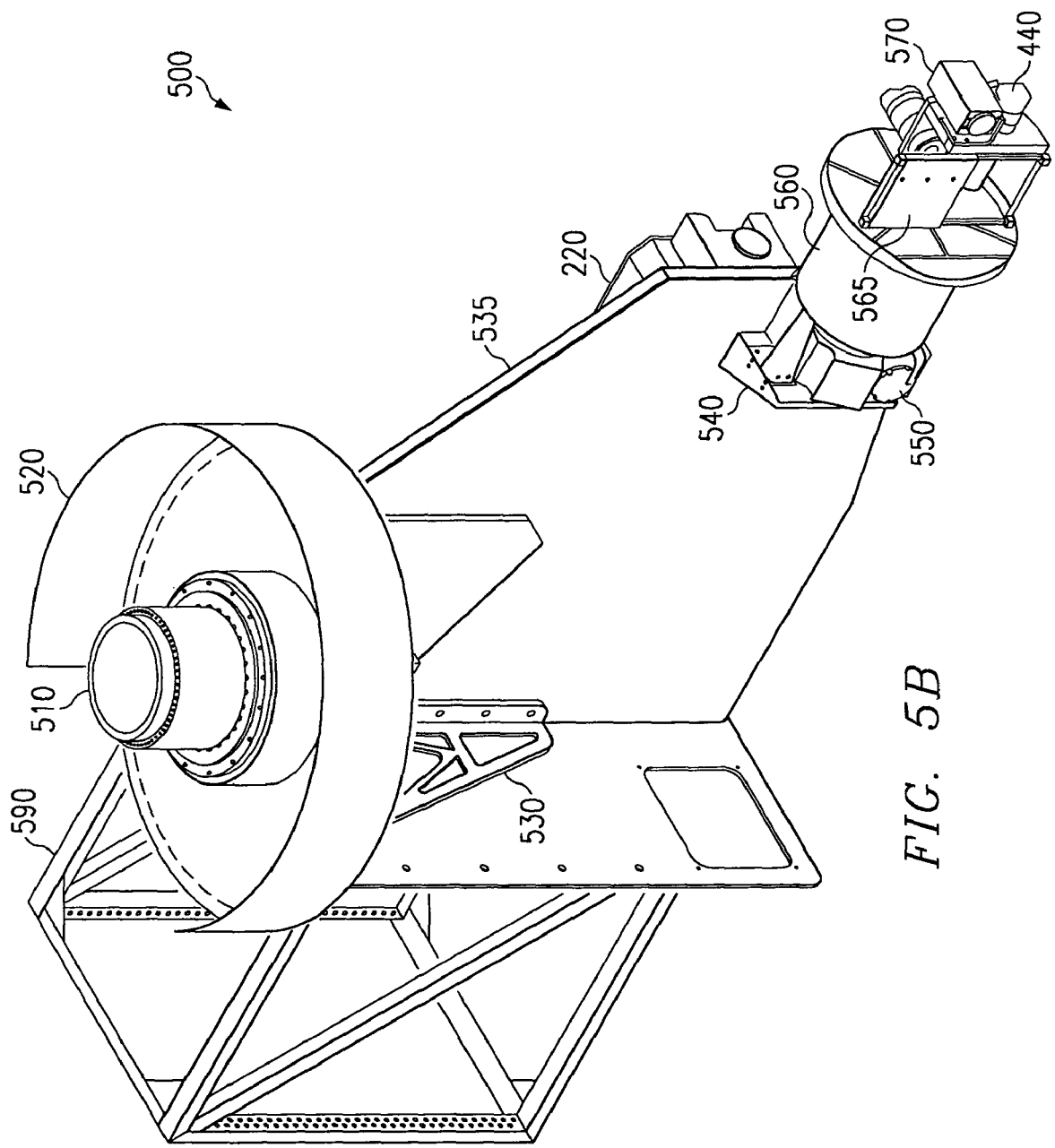
FIG. 5B presents a gantry mounted optical test apparatus with an internal calibration unit.

FIG. 5B illustrates scan head 500 in a perspective view with the addition of the detection laser mounted to the rear surface of optical table 535. In this configuration the detection laser beam 121 may be optionally fiber optic coupled to the front side of optical table 535 or directly coupled via turning mirrors. Fiber delivery via detection laser focusing optics 320 has the advantage of improved beam pointing stability due to the decoupling of any small beam pointing errors in laser 220. The peak power of laser 220 will limit the distance that fiber optics can be used to deliver beam 121 due to stimulated Brillouin scattering (SBS) effects. SBS threshold is dependent on the fiber diameter, fiber length, laser pulse duration, and laser peak power. For example, a Nd:YAG laser with a 100 microsecond pulse duration producing hundreds of watts of peak power would be limited to fiber lengths below 10 meters for 100 microm fiber diameters.

Figure 6:
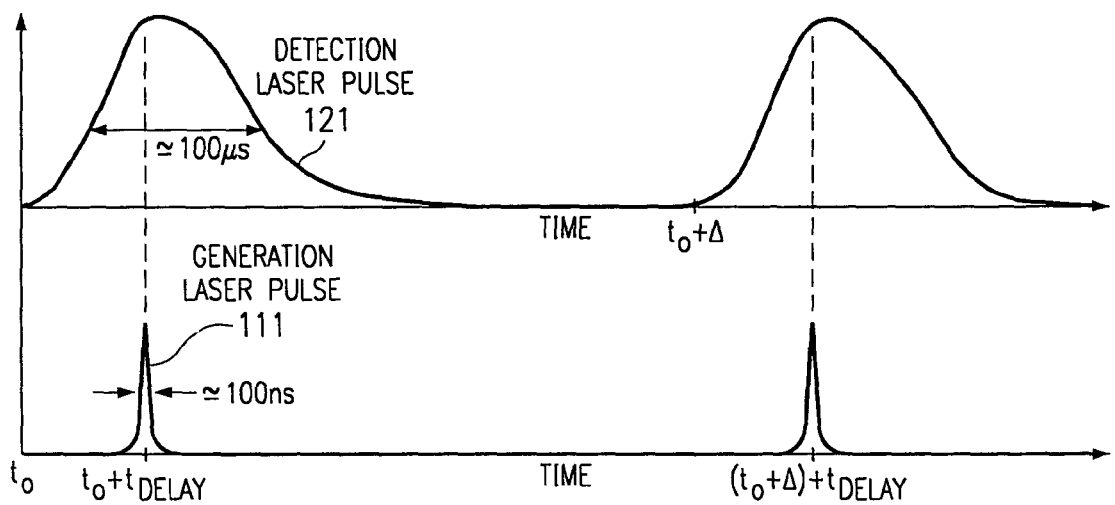
FIG. 6 is a timing diagram for a non-flat detection pulse and a generation pulse.

FIG. 6 illustrates the timing relationship between the generation and detection laser pulses. Detection laser beam 121 is fired at $t=t_0$. The magnitude of detection laser beam 121 rises to a maximum before falling off. The pulse width of detection laser beam 121 and generation laser beam 111 are illustrated in FIG. 6 as 100 micro-seconds and 100 nS, respectively, though the pulse widths may be varied. Generation laser beam 111 is ideally fired when detection laser beam 121 is at or near its maximum peak, which time delay after $t_0$ is represented by $t_{delay}$. When testing a target 150, detection and generation pulses are typically repeated on a periodic basis, for example, with a frequency of 100 Hz or even 1000 Hz where optical scanner 440 indexes the laser beam to a new position between each pulse. Ideally, the time delay Δ between subsequent pulses is sufficient to allow ultrasonic activity to dissipate so that there is no overlap between subsequent tests.

Figure 7:
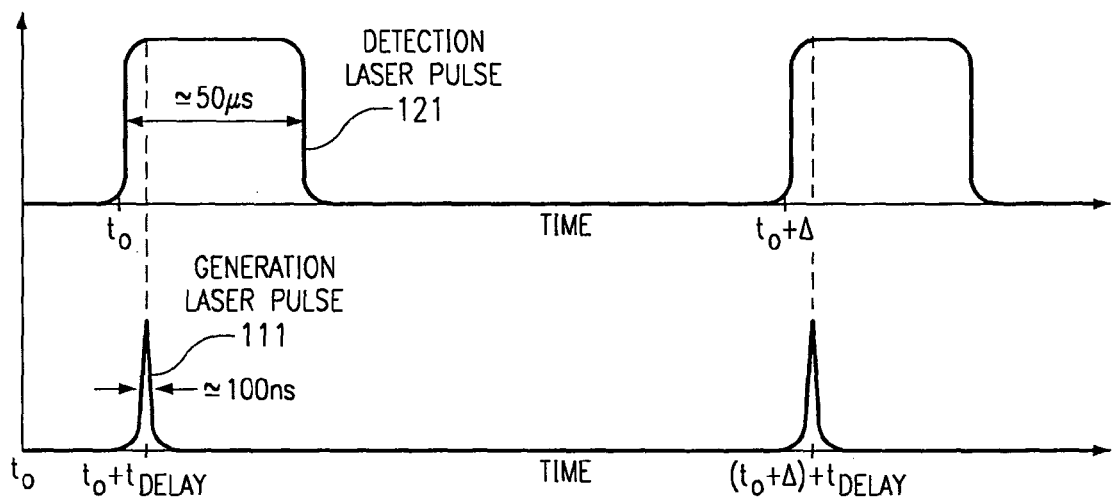
FIG. 7 is a timing diagram for a flat detection pulse and a generation pulse.

FIG. 7 illustrates that detection laser beam 121 may also be a flat pulse beam as shown in FIG. 7. By using a flat pulse detection laser, the time delay $t_{delay}$ between detection laser beam 121 and generation laser beam 111 can be reduced because a flat pulse beam requires less time to reach its maximum intensity.

FIG. 8 illustrates a confocal Fabry-Perot interferometer which is stabilized using only the input signal. The self-referenced feature is unlike many prior art designs which utilizes a portion of the generation laser beam for stabilization. In FIG. 8 incoming light from a fiber optic input is directed through a first lens 810 onto a first reflective surface 850, off a second reflective surface 860, through a first polarized beam splitter 840, through a quarter-wavelength plate 870, and into a first cavity 895. First cavity 895 has a confocal lens structure comprised of a first spherical mirror 875 and a second spherical mirror 885. When the incoming light passes through first polarized beam splitter 840, only the horizontally-polarized component is passed, which component becomes circularly polarized (p-state) once it passes through quarter-wavelength plate 870.

The confocal lens structure is designed so that the incoming light falls upon itself after four passes through the cavity. First spherical mirror 875 and second spherical mirror 885 each have the same radius of curvature "r", and when the two mirrors are spaced from each other by this radius "r", the mirrors are said to be in a confocal position, and the light is said to be "re-entrant light" because it falls back upon itself after four passes across the mirrors. First spherical mirror 875 and second spherical mirror 885 are partially transmissive, meaning they pass light as well as reflect light. For example, the said mirrors may be 95% reflective and 57% ignoring absorption and scattering losses, transmissive (i.e. permitting 55% of the light to pass through the mirror).

Some of the incoming light is transmitted through second spherical mirror 885. A third lens 830 focuses the light that is transmitted through second spherical mirror 885 upon transmission-mode detector 890 or optionally an optical fiber attached to transmission mode detector 890, where it can be quantified by variable $V_{T1}$. Second spherical mirror 885 also reflects a portion of the light back upon first spherical mirror 875, where again, some of the light is passed through spherical mirror 875, and through quarter-wavelength plate 870. When the reflected light passes through quarter-wavelength plate 870 for the second time, the polarization of the light is changed again, and in this case, becomes vertically polarized (s-state). The vertically polarized, reflected light is then rejected by first polarized beam splitter 840 and is reflected upon second lens 820, which focuses the reflected light upon a reflection-mode detector 880 or optionally an optical fiber attached to reflection-mode detector 880, where it can be quantified by variable $V_{R1}$.

It is possible to vary the amount of light which is transmitted through the cavity relative to the amount of light which is reflected back through the cavity, that is, vary $V_{T1}$ relative to $V_{R1}$. One way to vary this relationship is by changing the frequency of the incoming light. An alternative way to vary the relationship is by adjusting the distance between first spherical mirror 875 and second spherical mirror 885. In a confocal relationship, this distance is nominally the radius of curvature "r". One way to vary this distance is to mount at least one of the spherical mirrors on adjustable mounts. In FIG. 8, first spherical mirror 875 is mounted on piezoelectric mounts 876, which permits the lineal displacement of first spherical mirror in a controlled fashion using a piezoelectric device. The design of the present invention permits the distance between first spherical mirror 875 and second spherical mirror 885 to be increased by an additional amount "n", representing a small sub-wave length lineal displacement of first spherical mirror 875 by the piezoelectric device. Thus, the distance between the spherical mirrors can be represented by formula r+n. In FIG. 8, second spherical mirror 885 is mounted on manual mounts 886 to permit manual adjustment. Manual mounts 886 permit the cavity to be adjusted during setup for a "rough" adjustment to establish the correct confocal length, where for example, the length r must be within 200 microns of the desired length for a 1000 mm cavity. This feature when combined with the fine tuning using the piezoelectric device, provides the invention with significant flexibility.

FIG. 9 illustrates a confocal Fabry-Perot interferometer having two cavities, again which is stabilized using only the input light. The first cavity 895 in this configuration functions the same as the cavity described in connection with FIG. 8, and therefore, only the differences will be described here.

In FIG. 9 incoming light is directed onto first polarized beam splitter 840, where the light is divided into its horizontally-polarized (p-state) component and its vertically-polarized (s-state) component. One polarization of light is directed into first cavity 895, while the other polarization is directed into a second cavity 995. To be consistent with FIG. 8, the horizontal component is directed into first cavity 895 while the vertical component is reflected upward where it will be ultimately diverted into second cavity 995. The vertically polarized light travels from the first polarized beam splitter 840 to a second polarized beam splitter 940, where the light is reflected through a quarter-wavelength plate 970. The vertically-polarized light becomes circularly polarized once it passes through quarter-wavelength plate 970. The light is subsequently delivered into second cavity 995, where as in the first cavity 895, some of the light is transmitted through while some is reflected back.

As in the first cavity, first spherical mirror 975 and second spherical mirror 985 each have the same radius of curvature "r" (which is the same radius of curvature as in the first cavity 995), such that when the two mirrors are spaced from each other by this radius "r", the mirrors refocus incoming light upon itself after it travels four passes through the cavities (i.e., two round trips).

The light that is transmitted through second spherical mirror 985 is focused by third lens 930 upon transmission mode detector 990 or optionally an optical fiber attached to transmission-mode detector 990, where it can be quantified by variable $V_{T2}$. Second spherical mirror 985 also reflects a portion of the light back upon first spherical mirror 975, where again, some of the light is passed through spherical mirror 975, and through quarter-wavelength plate 970. When the reflected light passes through quarter-wavelength plate 970 for the second time, the polarization of the light is changed again, and in this case, becomes horizontally polarized. The horizontally polarized, reflected light then passes through polarized beam splitter 940, and is focused by second lens 920 upon reflection-mode detector 980 or optionally an optical fiber attached to reflection mode detector 980, where the reflected light can be quantified by variable $V_{R2}$.

It is possible to vary the amount of light which is transmitted or passes through each of the cavities relative to the amount of light which is reflected back through each of said cavities, that is, vary $V_{T1}$ relative to $V_{R1}$, and vary $V_{T2}$ relative to $V_{R2}$. One way to vary this relationship is by changing the frequency of the incoming light. An alternative way to vary the relationship is by adjusting the distances between first spherical mirrors 875 and 975 and second spherical mirror 885 and 985, respectively. In a confocal relationship, each of these distances is nominally the radius of curvature "r". One way to vary this distance is to mount at least one of each pair of spherical mirrors on adjustable mounts. In FIG. 9 each of first spherical mirrors 875 and 975 is mounted on piezoelectric mounts 876 and 976, respectively, which permits the sub-wavelength lineal displacement of first spherical mirrors 875, 975 in a controlled fashion using piezoelectric devices. The design of the present invention permits the distances between first spherical mirrors 875, 975 and second spherical mirrors 885, 985, respectively, to be increased by additional amounts "$\epsilon_1$" and "$\epsilon_2$", representing the lineal displacements of each of first spherical mirrors 875, 975 by piezoelectric means. Thus, the distances between the spherical mirrors within each cavity can be represented by formula r+$\epsilon_1$ and r+$\epsilon_2$. In FIG. 9, each of second spherical mirrors 885, 985 is mounted on manual mounts 886, 986, respectively, to permit manual adjustment. Manual mounts 886, 986 permit the cavity to be adjusted during setup for a "rough" adjustment to within a few hundred microns of the true confocal length, which when combined with the fine tuning using the piezoelectric means, provides the invention with significant flexibility.

Figure 10:
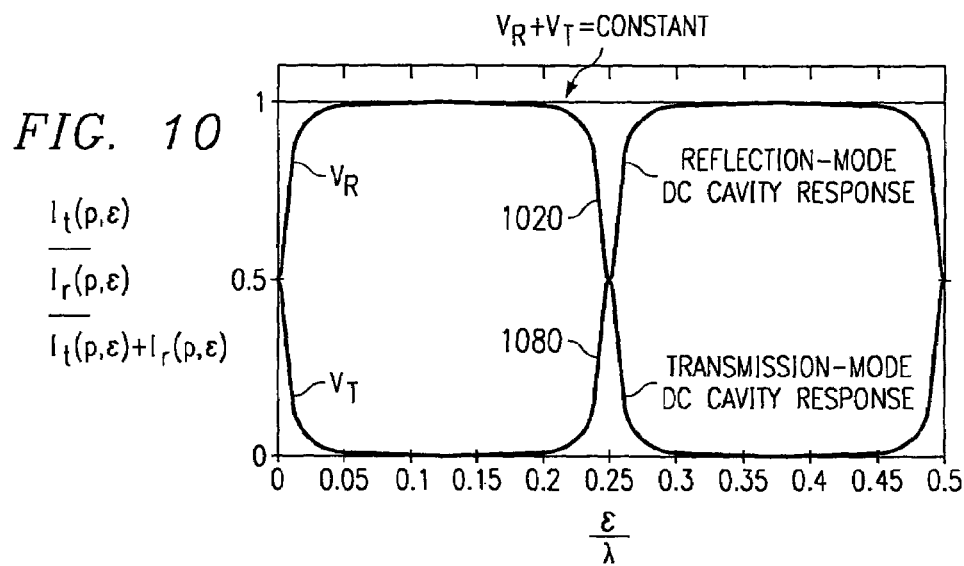
FIG. 10 illustrates the relationship between the reflected and transmitted light, relative to the total amount of light which reaches a cavity.

FIG. 10 demonstrates the relationship between the amount of light transmitted through a confocal cavity ("$V_T$"), the amount of light reflected back through the cavity ("$V_R$"), and the fine tuning adjustment represented by $\epsilon$. The normalized intensity of the transmitted and reflected light can be described in equation form by first defining two general complex (i.e. containing imaginary terms) functions as follows:

$$\beta(x) = \frac{T}{1 - R^2 e^{-ix}}$$

$$\gamma(x) = 1 - R\beta(x)e^{-ix}$$

where R is the mirror reflectivity and T is the mirror transmission usually given by T=1–R if absorption and scattering effects are ignored. Now the intensity of the light can be written as:

$$\text{transmission} = (1 - R^2)\left|\beta\left(2\pi\varepsilon\frac{4}{\lambda}\right)\right|^2$$

$$\text{reflection} = R\left[\left|\gamma\left(2\pi\varepsilon\frac{4}{\lambda}\right)\right|^2 + \left|\beta\left(2\pi\varepsilon\frac{4}{\lambda}\right)\right|^2\right]$$

where epsilon is the change in the cavity length from the confocal length r and lambda is the laser wavelength, and the magnitude operations on the complex function makes the results real expressions. These two equations will produce FIG. 10. Where the reflected light curve 1020 represents the proportion of total light that is reflected back through the cavity, (normalized reflection=$V_R/(V_R+V_T)$), which figure is always between 0.5 and 1.0. Transmitted light curve 1080 represents the proportion of total light that is transmitted through the cavity, (normalized transmission=$V_T/(V_R+V_T)$), which figure is always between 0.0 and 0.5. The sum of $V_R$ and $V_T$ represents the total amount of light that reaches the cavity. Reflected light curve 1020 and transmitted light curve 1080 are each plotted as a function of ε/S, and $V_R$, and $V_T$ are both equal when ε/S is equal to 0, 0.25, and 0.5, or more generically, when ε/S=n/4, n being a whole number. Thus it is apparent that the piezoelectric mirror mounts 876 and 976 must move a minimum of λ/4 to provide a sufficient tuning range.

While FIG. 10 is plotted for $V_R$, and $V_T$ (normalized, of course, with respect to the total amount of light), a similar relationship holds with respect to the variables $V_{R1}$, $V_{T1}$, $V_{R2}$, and $V_{T2}$ which were discussed in connection with FIGS. 8 and 9. While $\epsilon_1$ and $\epsilon_2$ are generally independent of each other in the two confocal cavity design, $\epsilon_1$ and $\epsilon_2$ are generally adjusted to maintain the same relationships between reflected and transmitted light in each of the cavities. For example, the cavities can be adjusted on a pulse-by-pulse basis to maintain the following relationship:

$$\frac{V_{T1}}{V_{R1} + V_{T1}} = \frac{V_{T2}}{V_{R2} + V_{T2}} = \eta(\text{constant})$$

wherein the constant η is a real number between 0.0 and 0.5 By fixing the relationship between the reflected light and transmitted light in each cavity in the two cavity designs, the incoming light can be quantitatively processed utilizing the known relationship between the signals of each cavity. A typical operating point would be for η=0.25, thereby 25% of the light would be transmitted through the interferometer and 75% reflected, and would represent an operating point half way along each resonance curve. It is evident from FIG. 10 that the above relationship can be satisfied for two distinct cases: either below the resonance peak or above it thereby changing the polarity of the detected signals.

The present design permits the interferometer to be self-stabilized utilizing exclusively the light which is delivered to the interferometer. Variations in the intensity of the incoming light, which typically are associated with each minute change in positioning of the surface being tested, have little or no impact on the functionality of the interferometer because the signals are based on percentages of light reflected or transmitted with respect to the total amount of light, and thus, are, in effect, normalized for the intensity of the incoming light. It may not be necessary to adjust the cavity tuning position on each laser pulse depending on the drift rate of the laser and the thermal stability of the interferometer. For example at a 400 Hz pulse rate adjustments could be made on every $10^{th}$ pulse or even less frequently depending on the environment and design. The present invention also uses algorithms based on absolute light intensity to suspend adjustment operations if the light level is too low, thereby preventing erroneous adjustments when the laser beams are off the target and tuning is impossible. When operated in conjunction with pulsed detection lasers it is typical that some form of peak-detection circuitry be employed to hold the peak values constant while a low-speed analog-to-digital converter samples the two or four channels of data. The drive voltage to each of the piezoelectric mirror mounts 876 and 976 is adjusted to compensate for any error based on the previous pulse. Reset of the peak detectors occurs prior to the next pulse. An electo-optic intensity controller (not shown) is typically used to limit the maximum light level sent to lens 810 and subsequently to detectors 880, 890, 980, and 990 thereby preventing damage to the detectors or signal electronics. The information used to control the light level is extracted from the same data used to stabilize the interferometer. Again, based on the results of the prior pulse the appropriate voltage is projected for the next pulse.

In the present invention having a two cavity design, substantially all of the incoming light is utilized for both stabilization and detection. Additionally, the second cavity permits a second set of signals that can be used to improve signal strength.

The output signal from an interferometer in connection with the detection of ultrasonic surface displacements, where the displacement u<<lambda can be represented with the following equation:

$$s(t) = u(t)*r(t) + a(t)*r'(t) + n(t)$$

where "s" represents the overall signal being produced by the interferometer; "k" is the wavevector defined as $$k = \frac{2\pi}{\lambda};$$

"u" represents the ultrasonic surface displacements being measured (i.e., the desired signal); "r-prime" represents the response function of the interferometer; "a" represents the laser noise (e.g., amplitude fluctuation); "r" represents the response function of the interferometer to the laser noise, which may be different from the response to an input signal; and "n" represents noise in the detection process (e.g., shot noise, electronic thermal noise, etc.).

The complex response functions of a confocal Fabry-Perot interferometer to an ultrasonic signal with a frequency $\omega_u = 2\pi f_u$ or amplitude noise fluctuation $\omega_n = 2\pi f_n$ can be defined with the following equations:

$$r_{T-mode}(\omega_u) = -i\left(\frac{\beta(\omega\tau + \omega_u\tau)}{\beta(\omega\tau)} - \frac{\overline{\beta(\omega\tau + \omega_u\tau)}}{\overline{\beta(\omega\tau)}}\right)\left(e^{-i\omega_u\frac{\tau}{4}} + R^2 e^{-i\omega_u\frac{3\tau}{4}}\right)\left(\frac{1}{1+R^2}\right)$$

$$r'_{T-mode}(\omega_n) = \left(\frac{\beta(\omega\tau + \omega_n\tau)}{\beta(\omega\tau)} - \frac{\overline{\beta(\omega\tau + \omega_n\tau)}}{\overline{\beta(\omega\tau)}}\right)\left(e^{-i\omega_n\frac{\tau}{4}} + R^2 e^{-i\omega_n\frac{3\tau}{4}}\right)\left(\frac{1}{1+R^2}\right)$$

$$r_{R-mode}(\omega_u) = -i\frac{\left[\overline{\gamma(\omega\tau)}\gamma(\omega\tau + \omega_u\tau) + \overline{\beta(\omega\tau)}\beta(\omega\tau + \omega_u\tau)e^{-i\omega_u\frac{\tau}{2}} - \gamma(\omega\tau)\overline{\gamma(\omega\tau + \omega_u\tau)} - \beta(\omega\tau)\overline{\beta(\omega\tau + \omega_u\tau)}e^{i\omega_u\frac{\tau}{2}}\right]}{[|\gamma(\omega\tau)|^2 + |\beta(\omega\tau)|^2]}$$

$$r'_{R-mode}(\omega_n) = \frac{\left[\overline{\gamma(\omega\tau)}\gamma(\omega\tau + \omega_n\tau) + \overline{\beta(\omega\tau)}\beta(\omega\tau + \omega_n\tau)e^{-i\omega_u\frac{\tau}{2}} - \gamma(\omega\tau)\overline{\gamma(\omega\tau + \omega_n\tau)} - \beta(\omega\tau)\overline{\beta(\omega\tau + \omega_n\tau)}e^{i\omega_n\frac{\tau}{2}}\right]}{[|\gamma(\omega\tau)|^2 + |\beta(\omega\tau)|^2]}$$

Where the same substitutions for the beta and gamma functions as defined previously have been used to simplify the equations. In the above equations $\tau = 4r_{mirror}/c$ is the cavity round trip delay for mirrors of radius "$r_{mirror}$" and c is the speed of light. Finally the cavity tune position is defined by $$\omega\tau = \sqrt{\frac{1-\eta}{\eta}}\left(\frac{1-R^2}{R}\right)$$

where $\eta$ is the linear tune position between 0 and 0.5 as introduced previously, with 0.25 representing a position halfway along the resonance curve.

If a signal is generated for both the reflected and transmitted components of a confocal cavity, the two signals can be represented as follows:

$$S_1(t) = U_1(t) * r_1(t) + a_1(t) * r_1'(t) + n_1(t)$$

$$S_2(t) = U_2(t) * r_2(t) + a_2(t) * r_2'(t) + n_2(t)$$

where, for example, $S_1$ represents the light that has been transmitted through the cavity, and $S_2$ represents the light that has been reflected back through the cavity.

Because the input signal is the same for each formulae, $U_1 = U_2$ and $a_1 = a_2$. These relationships are true because the ultrasonic surface displacements and the laser noise are independent of the reflection and transmission modes. Therefore, the two equations can be rewritten as follows:

$$S_1(t) = U(t) * r_1(t) + a(t) * r_1'(t) + n_1(t)$$

$$S_2(t) = U(t) * r_2(t) + a(t) * r_2'(t) + n_2(t)$$

Ideally, the two modes of the cavity have the same response functions with respect to signal "u", but the responses are negatives of each other because the transmission and reflection modes have opposite response slopes. Hence, $r_1 + r_2 = 0$. Ideally, with respect to the laser noise, $r_1' = r_2'$. Each response function must be normalized in regard to the tune position of the interferometer and is implicitly corrected to indicate a balanced response between the two modes. For example the if the transmission tune position is at 25% then the reflection is at 75% and a 3× normalization correction factor is used. And, if the signals are used to create a differential, the following relationship results (dropping the time notation):

$$S_2(t) = U(t) * r_2(t) - a(t) * r_2'(t) - a(t) * r_1'(t) + n_2(t) - n_1(t)$$

Dropping the time aspect, for ease of representation, and making the substitutions results in:

$$s_2 - s_2 = u * r_2 - u * r_1 + a * r_2' - a * r_1' + n_2 - n_1$$

$$= u * r_1 - u * r_1 + a * r_1' - a * r_1' + n_2 - n_1$$

$$= -2u * r_1 + n_2 - n_1$$

Hence, by using a differential signaling scheme, the common mode laser noise can be eliminated. Even if the stated conditions relating to $\{r_1, r_2\}$ and $\{r_1', r_2'\}$ are not perfectly met, the differential signaling scheme has the effect of removing substantially all common mode noise "a(t)".

Further, if $n_2$ is uncorrelated with $n_1$, then the two noise fluctuations will add incoherently and if the magnitudes of the two are substantially similar, $|n_1| = |n_2| = |n|$, we get:

$$S_2 - S_1 = 2(2k)u * r_2 + \sqrt{2}n$$

This is the same result one would arrive at by considering the process of averaging two signals with uncorrelated noise terms of equal magnitudes, where the noise will be increase by the square-root of the number of averages and the signal would increase in a linear manner.

1.4 in addition to the removal of common-mode laser noise. Each pair of signals for the two cavities is processed in a substantially similar manner to remove common-mode noise and then the two remaining signals can be further combined yielding another 1.4 increase in SNR.

Typically, the dominate noise source is from laser relaxation oscillations in solid state lasers and is characterized by the "relative intensity noise" or "RIN" of the detection laser. Reduction or elimination of laser RIN is essential for high SNR performance. In systems employing post collection optical amplification schemes, hetrodyne-mixing noise from signal and amplified spontaneous emission ("ASE") can also manifest as a common-mode noise source. Again, use of the self-referenced differential confocal Fabry-Perot interferometer can be used to minimize or eliminate such noise terms.

Figure 11:
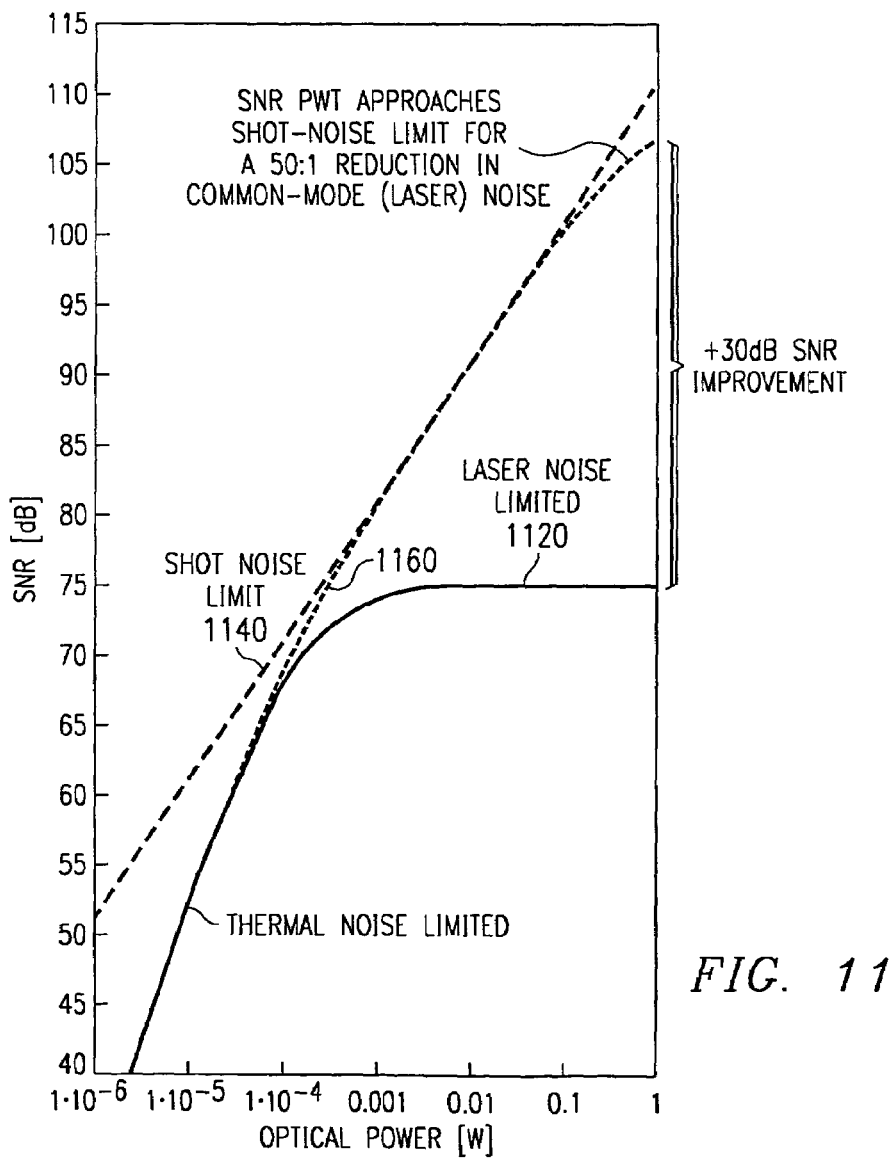
FIG. 11 is a signal-to-noise ratio plot as a function of optical power.

FIG. 11 demonstrates the significant improvement in SNR. In FIG. 11 the SNR plot 1120 illustrates the limits associated when common-mode laser produced noise "RIN" is not removed. Generally, when very little light is being delivered to the interferometer, thermal noise dominates and hence limits the SNR, which limitation is illustrated by the lower portion of single cavity SNR plot 1120. As the light being delivered to the interferometer is increased, the increase in SNR rolls off and becomes laser noise limited due to "RIN" effects, which limitation is illustrated by the upper portion of single cavity SNR plot 1120. Hence, in a typical single-mode processed confocal cavity interferometer, the SNR may at best be 75 dB. Moreover, above about 1 milliwatt, further increases in the amount of light being delivered to the interferometer are wasted because the laser noise dominates.

FIG. 11 also illustrates a differential SNR plot 1160, plotted as a function of optical power. As the light being delivered to the interferometer is increased, differential SNR plot 1160 generally increases and is limited only by shot noise limit 1140 (i.e., the internal noise associated with the detectors). Shot noise 1140 appears as a linear function on the logarithmic scale of FIG. 11. As differential SNR plot 1160 demonstrates, the ability to reduce the common mode laser noise results in a significant increase in SNR, and can be as much as 30 dB. Moreover, by increasing the amount of light being delivered to the interferometer, the SNR can be significantly improved.

Figure 12A:
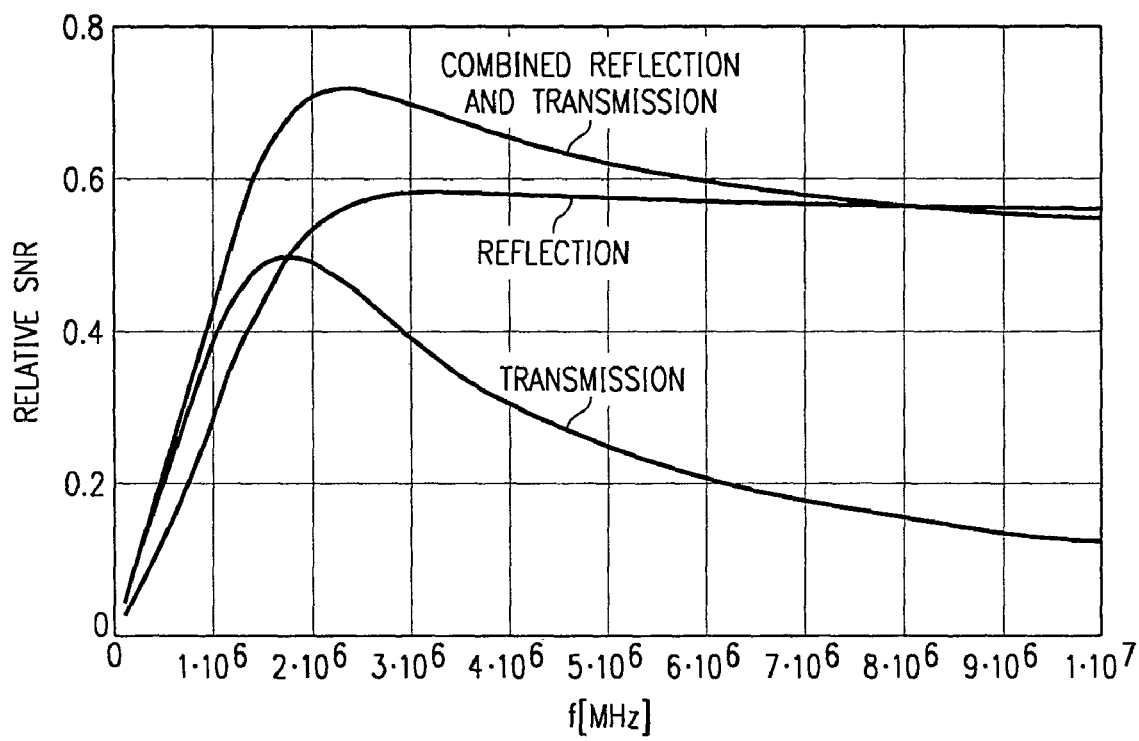
FIG. 12A is a signal response analysis as a function of frequency.
Figure 12B:
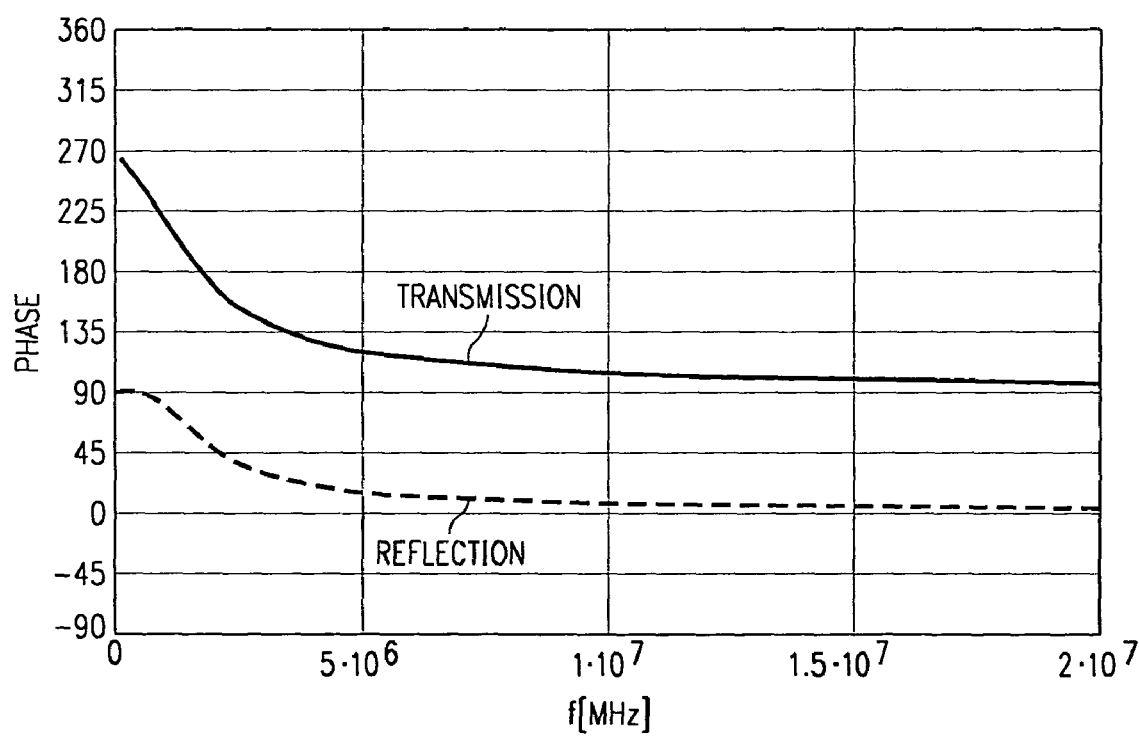
FIG. 12B is a phase response analysis for the signal presented in FIG. 12A.

FIGS. 12A and 12B present a signal response analysis for reflected signal, transmitted signal, and a combination of the two. FIG. 12A is a plot representative of the SNR of these signals as a function of frequency, while FIG. 12B presents the relative phase diagrams for each the reflected signal and transmitted signal, again as a function of frequency. These signals are related to $r_1(t)$ and $r_2(t)$, respectively, discussed above. These plots were generated using a confocal cavity having spherical mirrors that are 95% reflective spaced one (1.0) meter apart. FIG. 12A demonstrates that the SNR of the combined reflected and transmitted signal generally is higher than either component alone. FIG. 12B illustrates that over the frequency range on the abscissa, the phase difference between the transmitted signal and reflected signal changes gradually from approximately 180 degrees (i.e., completely out of phase) and levels out to approximately 90 degrees. Differences in phase must be considered when combining the transmitted and reflected signals from the cavities. This shows the expected result where at low frequency the response to signals follows the dc-response curve in FIG. 10, which clearly would represent a 180-degree phase shift between the two modes. The response at high frequencies is somewhat more complicated but is a known function as defined previously and can be deconvoluted from the measured signals for optimal processing results.

Figure 13A:
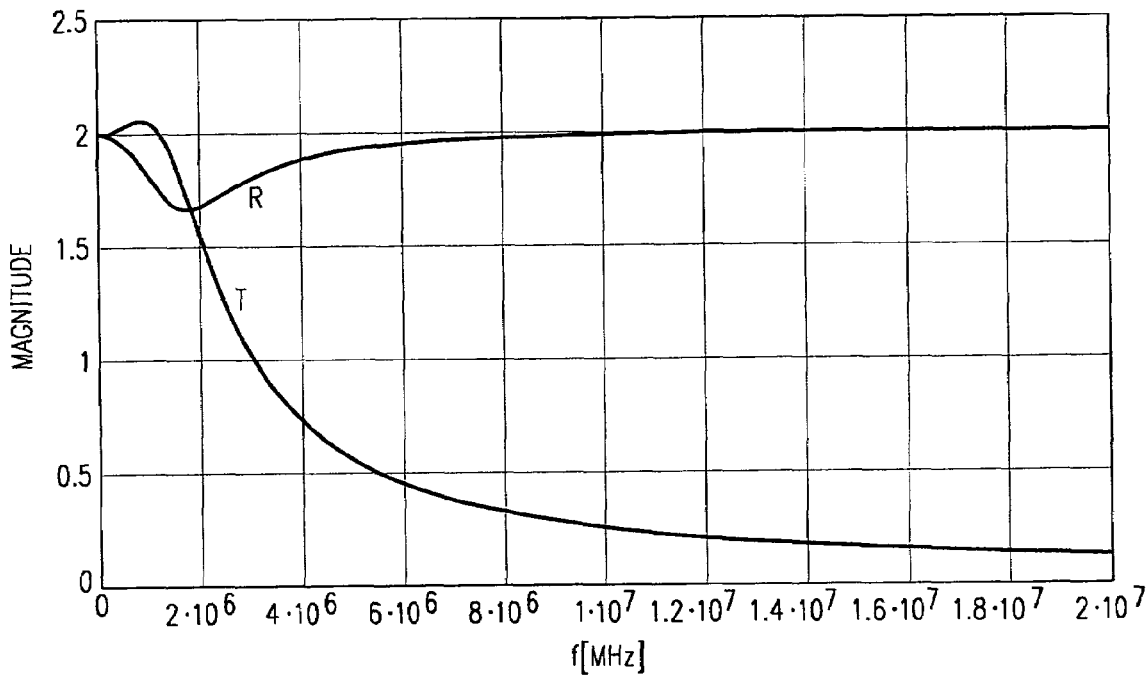
FIG. 13A is a noise response analysis as a function of frequency.
Figure 13B:
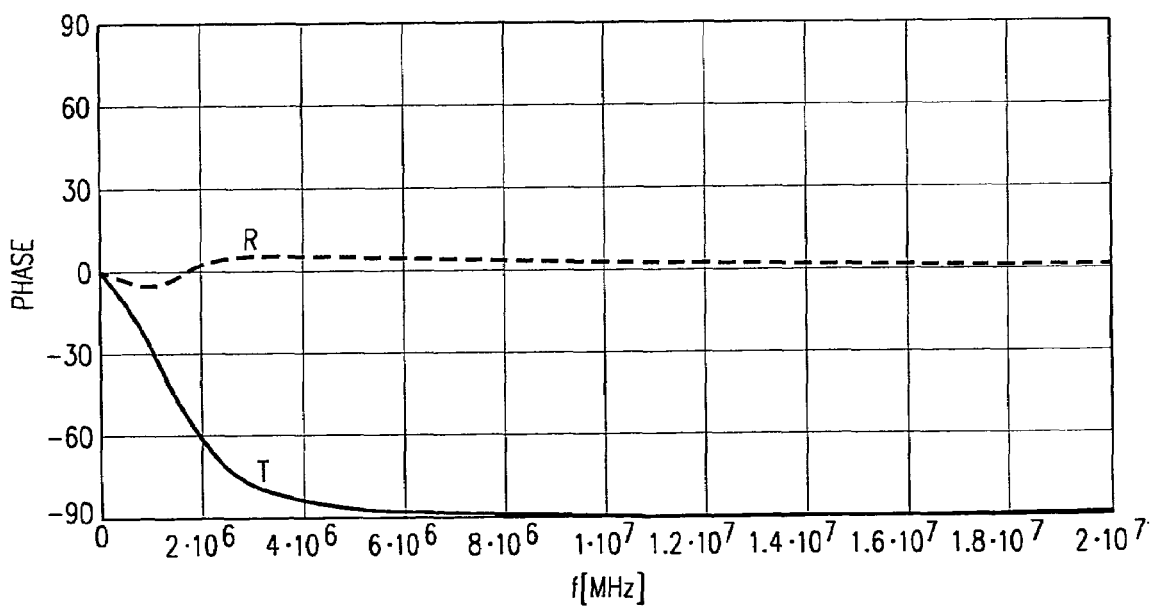
FIG. 13B is a phase response analysis for the information presented in FIG. 13A.

FIGS. 13A and 13B presents a noise response analysis for the interferometer's response to laser noise. FIG. 13A is a plot representative of the magnitude of reflected noise response and transmitted noise response as a function of frequency, while FIG. 13B presents the relative phase diagrams for the reflected noise and transmitted noise, again as a function of frequency. These plots were generated using a confocal cavity having spherical mirrors that are 95% reflective and being spaced one (1.0) meter apart. FIG. 13A demonstrates that for most frequencies, more noise is reflected than transmitted through the cavity. FIG. 13B illustrates that over the frequency range on the abscissa, the phase difference between the transmitted noise and reflected noise changes gradually from approximately 0 degrees (i.e., completely in phase) and levels out to approximately 90 degrees. Differences in phase must be considered when combining these outputs from the cavities.

Figure 14A:
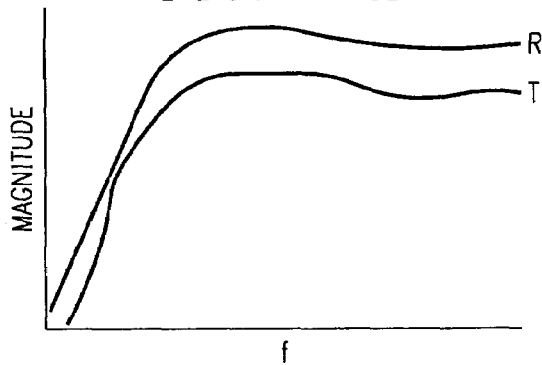
FIGS. 14(A and B) are a response analysis and the phase response for a signal that has been modified to permit cancellation of common mode laser noise.
Figure 14B:
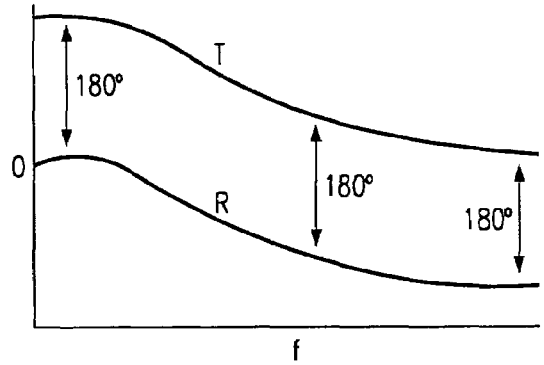

FIG. 14A represents a modified signal analysis, wherein the transmitted and reflected components have been modified to permit cancellation of the noise when the two components are subtracted. FIG. 14B illustrates that over most frequencies, the phase difference between the modified transmitted signal and reflected signal remains relatively constant at approximately 180 degrees (i.e., completely out of phase). This allows the two components to be subtracted for optimum noise reduction, while maintaining a significant level of signal. These plots show that transforming the data for maximum noise cancellation has the added benefit that signal is also improved.

In another embodiment of the present invention, the two confocal Fabry-Perot cavities can be self-referenced stabilized entirely with light present on the signal detectors such that the corresponding pair of transmitted and reflected intensities represent inverted responses to signals, yet remain in-phase to amplitude noise. This has the added advantage of removing common-mode noise without detailed knowledge of either the signal or noise response functions due to the substantially matched responses between the reflection and transmission for each cavity. Again, the resulting SNR enhanced pair of signals can be further combined to one signal, using the appropriate corrections for optimally combining the processed reflected and transmitted signals.

In one embodiment of the interferometer of the current apparatus, the detectors and the electronic circuitry used to monitor and adjust the cavities are integrated into the interferometer. When the detectors are integrated into the interferometer, there is a potential for introducing noise because the ground plane for the detector circuitry is separate from the ground plane for the data acquisition apparatus, and though the two planes may be connected, the distance between them permits the introduction of unwanted noise.

Figure 15:
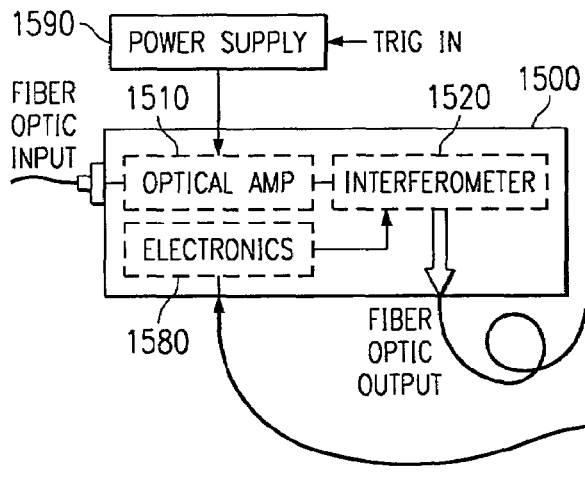
FIG. 15 presents an optical interferometer with separate detectors and processors.

FIG. 15 illustrates an alternative embodiment of an interferometer which is purely optical, and the detectors and the control circuitry are external, sharing a common ground plane with the data acquisition apparatus. In FIG. 15, the phase-modulated light is collected from the target and fed via fiber optics into electro-optical assembly 1500 comprised of optical amplifier 1510, optical interferometer 1520, and control electronics 1580. Optical interferometer 1520 is characterized by optical input and a plurality of optical outputs, though only one is shown in FIG. 15 for simplicity of presentation.

The output from optical interferometer 1520 is fed to a plurality of detectors 1540 which convert the optical input to analog signaling. The analog signaling is conditioned by analog signal conditioner 1550 and then captured and processed by digital signal processing ("DSP") unit 1560. DSP unit 1560 will compare $V_{R1}$ relative to $V_{r1}+V_{T1}$ and $V_{R2}$ relative to $V_{R2}+V_{T2}$ and determine whether adjustments are required in the cavities of optical interferometer 1520 to maintain the desired relationships, as previously discussed. If adjustments are required, then a digital output from DSP unit 1560 may be converted to analog by D/A unit 1570 and sent to electronic controller 1580, which makes the proper adjustments to optical interferometer 1520, for example, by adjusting the piezoelectric devices within the interferometer.

Optical amplifier 1510 functions on a pulse-by-pulse basis, and hence, a trigger signal is used in operation. The trigger signal may be provided indirectly, for example, through power supply 1590, or may be provided directly to optical amplifier 1510. In a real-time like fashion, the electronics process the optical signal to determine the amount of light that has been delivered to the interferometer. If the interferometer is saturated, then the gain is turned down inside optical amplifier 1510, and the interferometer is adjusted to operate in a more optimum range. If the interferometer is operating below an optimum light level, then the gain is turned up inside optical amplifier 1510, and the interferometer is again adjusted to operate in a more optimum range. As illustrated previously in FIG. 11, the SNR in the present design can be improved by increasing the light delivered to the interferometer. Increasing SNR is usually desirable. Moreover, because the stabilization scheme of the interferometer is independent of light intensity, varying the optical gain has little or no effect on the stabilization process of the interferometer.

Figure 16:
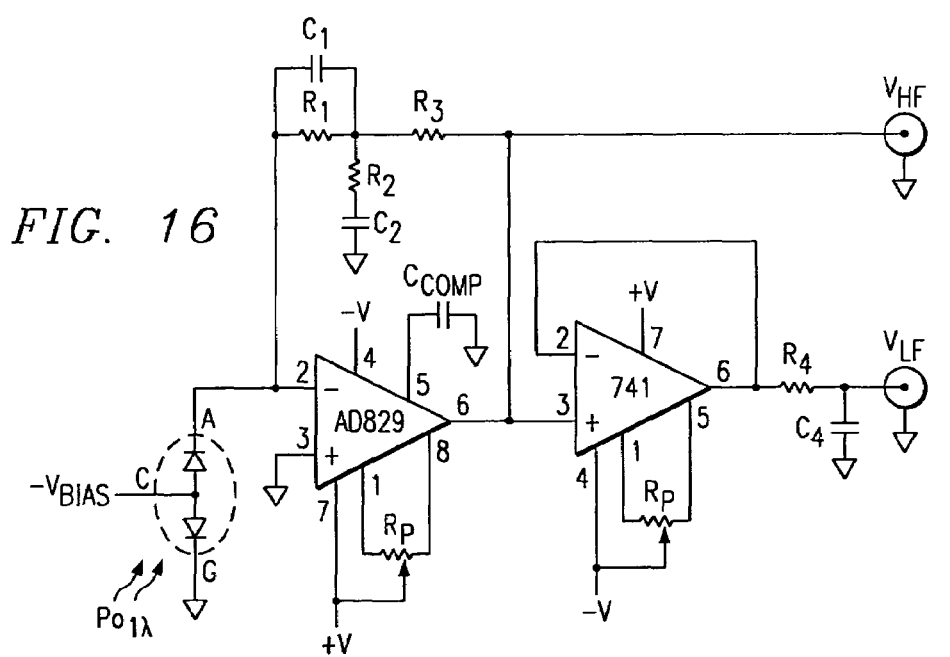
FIG. 16 is an electrical schematic for an improved detector.

FIG. 16 illustrates an electrical schematic for an improved detector. The detector must accommodate two very different inputs: 1) the large detection pulse; and 2) the tiny modulations riding on top of said pulse, containing information about the ultrasonic surface displacements. The large detection pulse must be converted into a dc signal so that the interferometer can be stabilized, while the tiny modulations must be separated for demodulation. The improved detector of FIG. 16 accommodates these two different signals with a single circuit through the use of a "T-feedback" loop, said "T" being formed by resistors R1, R2 and R3. This circuit provides a low gain response to the large pulse and a high gain response to the modulations.

Figure 17:
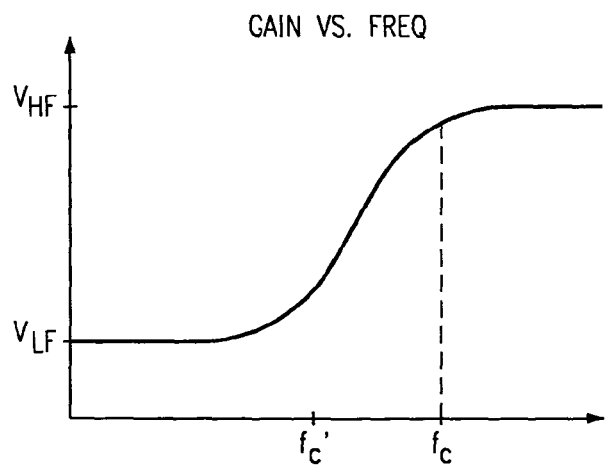
FIG. 17 is a frequency response for the electrical schematic of FIG. 16.

FIG. 17 illustrates the frequency response of the T-feedback loop.

While circuits other than those illustrated by FIG. 16 can be used to meet these needs, the circuit provided in FIG. 16 is a single circuit solution to the problem.

Although the present invention has been described in detail, it should be understood that various changes, substitutions and alterations can be made hereto without departing from the spirit and scope of the invention as defined by the appended claims.

What is claimed is:

1. An apparatus for generating and detecting ultrasonic surface displacements on a remote target comprising:
    a first pulsed laser to generate a first pulsed laser beam to illuminate a portion of a surface of the remote target and produce ultrasonic surface displacements substantially within the illuminated portion of the surface of the remote target;
    a second pulsed laser to generate a second pulsed laser beam coaxial with said first pulsed laser beam, wherein the second pulsed laser beam substantially illuminates the portion of the surface illuminated by the first pulsed laser beam to detect the ultrasonic surface displacements on the surface of the remote target;
    a scanning optical assembly operable to direct the first pulsed laser beam and second pulsed laser beam to the surface of the remote target;
    collection optics, optically coupled to the scanning optical assembly, operable to collect phase modulated light from the second pulsed laser beam either reflected or scattered by the remote target;
    an interferometer self-stabilized with the phase modulated light, wherein the interferometer is operable to process the phase modulated light and generate at least one output signal; and
    a processor operable to:
    process the at least one output signal to obtain data representative of the ultrasonic surface displacements on the surface of the remote target; and
    process the data representative of the surface displacements to assess the structural integrity of the remote target.

2. The apparatus of claim 1 further comprising an intensity controller to adjust on a pulse-by-pulse basis the intensity of the second pulsed laser beam in proportion to the intensity of the phase modulated light collected by the collection optics.

3. The apparatus of claim 1 wherein the first pulsed laser emits a laser beam of coherent light of about 10 microns in wave length.

4. The apparatus of claim 1 wherein the interferometer is self-stabilized using substantially 100% of the phase modulated light delivered to the interferometer by the collection optics.

5. The apparatus of claim 1 further comprising an optical ranging unit to calculate a distance by which the remote target is separated from the apparatus.

6. A large area composite inspection apparatus for measuring ultrasonic surface displacements on a surface of a remote target comprising:
    a detection laser to generate a pulsed laser beam to detect the ultrasonic surface displacements on the surface of the remote target;
    a scanning optical assembly operable to scan the pulsed laser beam across the surface of the remote target;
    collection optics, optically coupled to the scanning optical assembly for collecting phase modulated light from the pulsed laser beam either reflected or scattered by the remote target;
    an interferometer to process the phase modulated light collected by the collection optics, wherein the interferometer is self-stabilized with the collected phase modulated light either reflected or scattered by the remote target;
    said interferometer comprising:
    a first cavity having a first confocal lens structure; a second cavity having a second confocal lens structure; a device for dividing incoming de-polarized light into a first polarized light component and a second polarized light component wherein said device also directs said first and second polarized light components into the first and second cavities;
    a control system to adjust said first and second cavities such that a ratio of light transmitted through each cavity to light reflected back through each cavity remains substantially constant; and
    a processor to process the light transmitted through the first cavity, the light reflected back through the first cavity, the light transmitted through the second cavity, and the light reflected back through the second cavity, all in order to obtain data representative of the ultrasonic surface displacements on the surface of the remote target.

7. The large area composite inspection apparatus of claim 6 further comprising an intensity controller which adjusts on a pulse-by-pulse basis the intensity of the pulsed laser beam in proportion to the intensity of the phase modulated light collected by the collection optics.

8. The large area composite inspection apparatus of claim 6 further comprising a positioning apparatus to move the detection laser across the surface of the remote target and then record and index the data detected by the large area composite inspection apparatus.

9. The large area composite inspection apparatus of claim 6 wherein the positioning apparatus is a gantry positioning apparatus.

10. The large area composite inspection apparatus of claim 6 further comprising a generation laser to generate a pulsed laser beam to detect generate the ultrasonic surface displacements on the surface of the remote target.

11. The large area composite inspection apparatus of claim 6 wherein the generation laser and the detection laser coaxially apply laser beams to the surface of the remote target.

* * * * *